(12) United States Patent
Irie et al.

(10) Patent No.: US 7,893,609 B2
(45) Date of Patent: Feb. 22, 2011

(54) ORGANIC ELECTROLUMINESCENCE ELEMENT DEFECT INSPECTION APPARATUS, ORGANIC ELECTROLUMINESCENCE ELEMENT AND ORGANIC ELECTROLUMINESCENCE ELEMENT DEFECT INSPECTION METHOD

(75) Inventors: Kazunobu Irie, Tokyo (JP); Tetsuo Oosono, Tokyo (JP)

(73) Assignee: Toppan Printing Co., Ltd. (JP)

( * ) Notice: Subject to any disclaimer, the term of this patent is extended or adjusted under 35 U.S.C. 154(b) by 90 days.

(21) Appl. No.: 12/340,430

(22) Filed: Dec. 19, 2008

(65) Prior Publication Data
US 2009/0159817 A1    Jun. 25, 2009

(30) Foreign Application Priority Data
Dec. 25, 2007    (JP) .............................. 2007-331727

(51) Int. Cl.
*H01L 51/50* (2006.01)
(52) U.S. Cl. ........................... 313/504; 313/506; 445/24
(58) Field of Classification Search ................. 313/504, 313/506; 445/224
See application file for complete search history.

(56) References Cited
U.S. PATENT DOCUMENTS
2004/0207314 A1* 10/2004 Aitken et al. ................ 313/504
2005/0001545 A1* 1/2005 Aitken et al. ................ 313/512
2007/0170860 A1* 7/2007 Choi et al. ................... 313/512
2008/0054796 A1* 3/2008 Sung et al. ................... 313/504

FOREIGN PATENT DOCUMENTS
| JP | 2001-291585 | 10/2001 |
| JP | 2006-329819 | 12/2006 |
| JP | 2007-012357 | 1/2007 |

OTHER PUBLICATIONS
Tang et al., "Organic electroluminescent diodes", Appl. Phys. Lett. 51 (12), pp. 913-915 (1987).

* cited by examiner

*Primary Examiner*—Nimeshkumar D. Patel
*Assistant Examiner*—Mary Ellen Bowman
(74) *Attorney, Agent, or Firm*—Squire, Sanders & Dempsey (US) LLP

(57) ABSTRACT

One embodiment of the present invention is an organic electroluminescence element defect inspection apparatus wherein the apparatus brings in an optical image of a substrate to be inspected and detects a pattern defect of an organic luminescent layer on the substrate to be inspected. The above is performed after an organic luminescent layer is formed on a substrate in a method of manufacturing an organic electroluminescence element. The organic electroluminescence element includes at least one or more organic luminescent layers having a luminescence area, an anode which injects a hole into the organic luminescent layer and a cathode which injects an electrode into the organic luminescent layer on a substrate. And an optical source for obtaining an optical image from a substrate to be inspected is infra-red radiation.

3 Claims, 3 Drawing Sheets ered from a nozzle is spherical, when the ink droplet drops onto the substrate, the ink spreads in a circular shape. Therefore, the shape of the pattern which is formed lacks linearity. In another case, since the accuracy of the point where the ink droplet is dropped is poor, there is a problem in that a linear pattern can not be obtained. On the other hand, for example, in Japanese Patent Laid-Open No. 2002-305077 Official Gazette, a method for forming a linear pattern by the following processes is disclosed: a bank having an ink-repellent property is formed on a substrate by a photolithography method or the like; thereafter, an ink droplet is dropped on the substrate and the ink is repelled according to the shape of the bank and a linear pattern is formed. However, when the repelled ink returns inside a picture element, the ink builds up. Thereby there remains a problem in that a fluctuation of film thickness of an organic luminescent layer inside a picture element occurs.

ORGANIC ELECTROLUMINESCENCE ELEMENT DEFECT INSPECTION APPARATUS, ORGANIC ELECTROLUMINESCENCE ELEMENT AND ORGANIC ELECTROLUMINESCENCE ELEMENT DEFECT INSPECTION METHOD

CROSS REFERENCE

This application is based upon and claims the benefit of priority from the prior Japanese Patent Application No. 2007-331727, filed on Dec. 25, 2007, the entire disclosure of which is incorporated herein by reference.

BACKGROUND OF THE INVENTION

1. Field of the Invention

The present invention relates to an inspection apparatus which is used for a defect inspection performed during a process of manufacturing an organic electroluminescence element and an electroluminescence element suitable for this defect inspection apparatus.

2. Description of the Related Art

An organic electroluminescence element is a luminescence element having a structure including an organic luminescent layer sandwiched between an anode and a cathode. By applying a voltage, a hole and an electron are injected from an anode and a cathode respectively. An electroluminescence element is an element in which energy generated by recombining the pair of the hole and the electron on the surface of an organic electroluminescence layer or within an organic electroluminescence layer is emitted as light. Although an organic electroluminescence element using an organic substance for a luminescent layer had been researched since long ago, there was no progress of a practical application due to problems of low luminescent efficiency. Whereas, an organic electroluminescence element having a laminated structure in which an organic layer was divided into two layers composed of a luminescent layer and a hole transport layer was proposed by C. W. Tang in 1987. Then, luminescence of high efficiency was confirmed under the condition of a low voltage (referred to as non-patent literature 1). Since that time, organic electroluminescence elements have been actively researched.

Organic materials used for a luminescent layer of an organic electroluminescence element are divided into a low molecular material and a high molecular material. A method of forming a luminescent layer varies according to the materials. For a low molecular material, a method for forming a film by an evaporation method is mainly used. For a high molecular material, a method for applying the high molecular material being dissolved or dispersed in a solvent on a substrate is used. And to make an organic electroluminescence element full colored, a luminescent layer is patterned. In the above patterning method, for a low molecular material, a method of evaporating and forming a luminescent material of different luminescent colors on a part corresponding to an intended picture element is performed and the method uses a mask on which a pattern corresponding to an intended picture element shape is formed. The above method is superior when a thin layer is evenly formed on an intended shape. However, a problem is that it becomes difficult to form a pattern in terms of accuracy of a mask when an evaporated substrate is large.

On the other hand, for a high molecular material, a pattern formation by an ink jet method and a pattern formation method by printing are mostly used. For example, an ink jet method disclosed in Japanese Patent Laid-Open No. H 10-12377 Official Gazette is the method of discharging a luminescent layer material dissolved in a solvent on a substrate from an ink jet nozzle and drying a luminescent layer material on the substrate to provide an intended pattern. However, since an ink droplet discharged from a nozzle is spherical, when the ink droplet drops onto the substrate, the ink spreads in a circular shape. Therefore, the shape of the pattern which is formed lacks linearity. In another case, since the accuracy of the point where the ink droplet is dropped is poor, there is a problem in that a linear pattern can not be obtained. On the other hand, for example, in Japanese Patent Laid-Open No. 2002-305077 Official Gazette, a method for forming a linear pattern by the following processes is disclosed: a bank having an ink-repellent property is formed on a substrate by a photolithography method or the like; thereafter, an ink droplet is dropped on the substrate and the ink is repelled according to the shape of the bank and a linear pattern is formed. However, when the repelled ink returns inside a picture element, the ink builds up. Thereby there remains a problem in that a fluctuation of film thickness of an organic luminescent layer inside a picture element occurs.

Then, an ink is made by using an organic high molecular luminescent material which is dissolved or dispersed in a solvent, instead of a low molecular organic luminescent material. A method for forming a pattern by a printing method using the ink has been proposed. In particular, a method performed by relief printing, a method performed by reverse type printing and a method performed by screen printing have been proposed. Especially, relief printing is superior in terms of accuracy of pattern formation and evenness of film thickness. Thereby, relief printing is suitable for a method for manufacturing an organic electroluminescence element performed by a printing method.

In the case of a pattern formation by a wet process such as an ink jet method and printing method, a process of forming a luminescent layer by patterning ink on a substrate is generally performed in air or in a nitrogen atmosphere. After this, ink is dried and a cathode is vacuum-evaporated by a vaporizing apparatus. Moreover, in the case of a top emission type element, an electrode can be made by sputtering instead of a vaporizing apparatus. And after a substrate undergoes a process of sealing and trimming, it becomes possible to activate and illuminate a panel by mounting a driving circuit.

However, when some failure occurs under a process of forming an organic luminescent layer and there is a defect in a pattern, until a driving circuit is attached and luminescence is confirmed, the failure is unperceivable. Furthermore, there is a case that a failure occurs continuously in all patterns of a formed luminescent layer depending on the content of a failure. In this case, in other words, at the stage where a defect in a panel is recognized, the substrates which underwent a process of forming an organic luminescent layer pattern after a substrate having a defect had undergone the process have all had a failure and loss of these substrates is a large problem.

As a solution to this problem, a manufacturing method in which a process loss is decreased is disclosed in Patent Document 1 JP-A-2001-291585. The method is as follows: an inspection is performed in a vacuum condition or a dried atmosphere between a process of evaporating an organic layer and an electrode on a substrate and a sealing process; and a defect can be discovered promptly. And in Patent Document 2 JP-A-2007-12357, a manufacturing method in which a process loss is decreased is disclosed as follows: the previous process is controlled by defect information taken after completion of a forming process by a roll to roll method, using an uninterrupted sheet-shaped substrate; with the above method, an additional process upon a defect generation point is omitted.

Clogging and a blot of a nozzle in an ink jet method and a blot of a plate, an anilox roll and a doctor blade in a printing method are examples of a continuously occurring failure. Thereby, after a luminescent layer is formed on a substrate, a defect inspection of a luminescent layer pattern on a substrate is performed as soon as possible and it is preferable that continuous generation of a defective substrate is prevented.

An optical inspection is performed broadly as an inspection method of a pattern formed on a substrate. An optical inspection determines whether a pattern formation is good or not by the following method: A pattern image on a substrate is taken in by a camera or a line sensor and next an image enhancement and a defect determination is performed. As a method of extracting a defect, an inspection method called die to die comparison, a method for practicing a contour definition and a method for practicing a comparison with an adjacent pattern are used. Among the above, a method for comparing with an adjacent pattern is suitable for an inspection of a substrate on which the same pattern lies regularly. And this method is used as a picture element defect inspection apparatus of a flat-panel display.

The light intensity of ultraviolet rays with which an inspection object of an interlevel product of an organic electroluminescence layer is irradiated to obtain an image is minimized. Therefore, degradation of an organic electroluminescence layer caused by an accumulative irradiance volume of ultraviolet lays generated at the time of an inspection is prevented. The above inspection method is disclosed in Patent document 3. However, a material used for an organic luminescent layer is very weak with an ultraviolet radiation and visible light under an oxygen presence. Then, a material is degraded by light irradiation. Therefore, even if an organic electroluminescence element is formed, a reduction in efficiency and lifetime occurs. Therefore, an optical inspection as shown in the above described method is not preferable.

Moreover, after a luminescent layer pattern is formed, a process of forming an electrode (a cathode) is performed by a vacuum process as shown above. Thereby, performing an optical inspection to avoid light irradiation in air is also possible after injecting a substrate into a vacuum chamber. However, in general, to make it possible that an optical effect inspection apparatus brings in an image of the whole surface of a substrate with one scan or a return scan to reduce inspection time, multiple cameras according to the size of the substrate, resolution and camera view are arranged in a line. Therefore, the apparatus required is large scale. Therefore, the dimensions of a vacuum chamber have to be large to install this defect inspection apparatus. Therefore, the optical defect inspection apparatus is not preferable, because the entire apparatus is expensive, including vacuum evacuation.

The present invention gave consideration to the above circumstances and a purpose of the present invention is to provide a defect inspection apparatus which performs a defect inspection of a luminescent layer pattern on a substrate as soon as possible after a luminescent layer is formed on the substrate, detects a substrate having a defect in a pattern formation by detecting a pattern defect of a luminescent layer and can improve productive efficiency. And the above are performed during a process of manufacturing an organic electroluminescence element. In addition, the purpose of the present invention is to provide an organic electroluminescence element suitable for the defect inspection apparatus.
[Patent Document1] JP-A-2001-291585
[Patent Document2] JP-A-2007-12357
[Patent Document3] JP-A-2006-329819
[Non-patent Document1]C. W. Tang, S. A. VanSlyke, Applied Physics Letters, Vol. 51, Page. 913, 1987.

SUMMARY OF THE INVENTION

One embodiment of the present invention is an organic electroluminescence element defect inspection apparatus wherein the apparatus brings in an optical image of an inspected substrate and detects a pattern defect of an organic luminescent layer on the inspected substrate. The above is performed after an organic luminescent layer is formed on a substrate in a process of manufacturing an organic electroluminescence element. The organic electroluminescence element includes at least one or more organic luminescent layers having a luminescence area, an anode injecting a hole into the organic luminescent layer and a cathode injecting an electrode into the organic luminescent layer on a substrate and an optical source for obtaining an optical image from an inspected substrate is infra-red radiation.

1 . . . an inspected substrate, 2 . . . a stage, 3 . . . a stage driving mechanism, 4 . . . an infra-red radiation optical source (a transmitted illumination), 5 . . . infrared light, 6 . . . a mirror, 7 . . . an infra-red radiation optical source (a reflected illumination), 9 . . . a half mirror, 10 . . . a lens, 11 . . . an image sensor, 12 . . . an image processing apparatus, 13 . . . an light interception enclosure, 14 . . . an inactive gas injecting hole, 20 . . . a substrate retainment section, 21 . . . an inactive liquid tank, 22 . . . an inactive liquid, 30 . . . an organic luminescent layer, 31 . . . a switching element, 32 . . . a metal wiring (a scanning line), 33 . . . a substrate material, 34 . . . a confining wall, 35 . . . a substrate, 36 . . . an anode (a picture element electrode), 37 . . . a cathode (an opposite electrode), 38 . . . a hole transport layer

DETAILED DESCRIPTION OF THE INVENTION

An organic electroluminescence element defect inspection apparatus of the present invention is explained below in detail with reference to the figures based on one embodiment.

Figure 1:
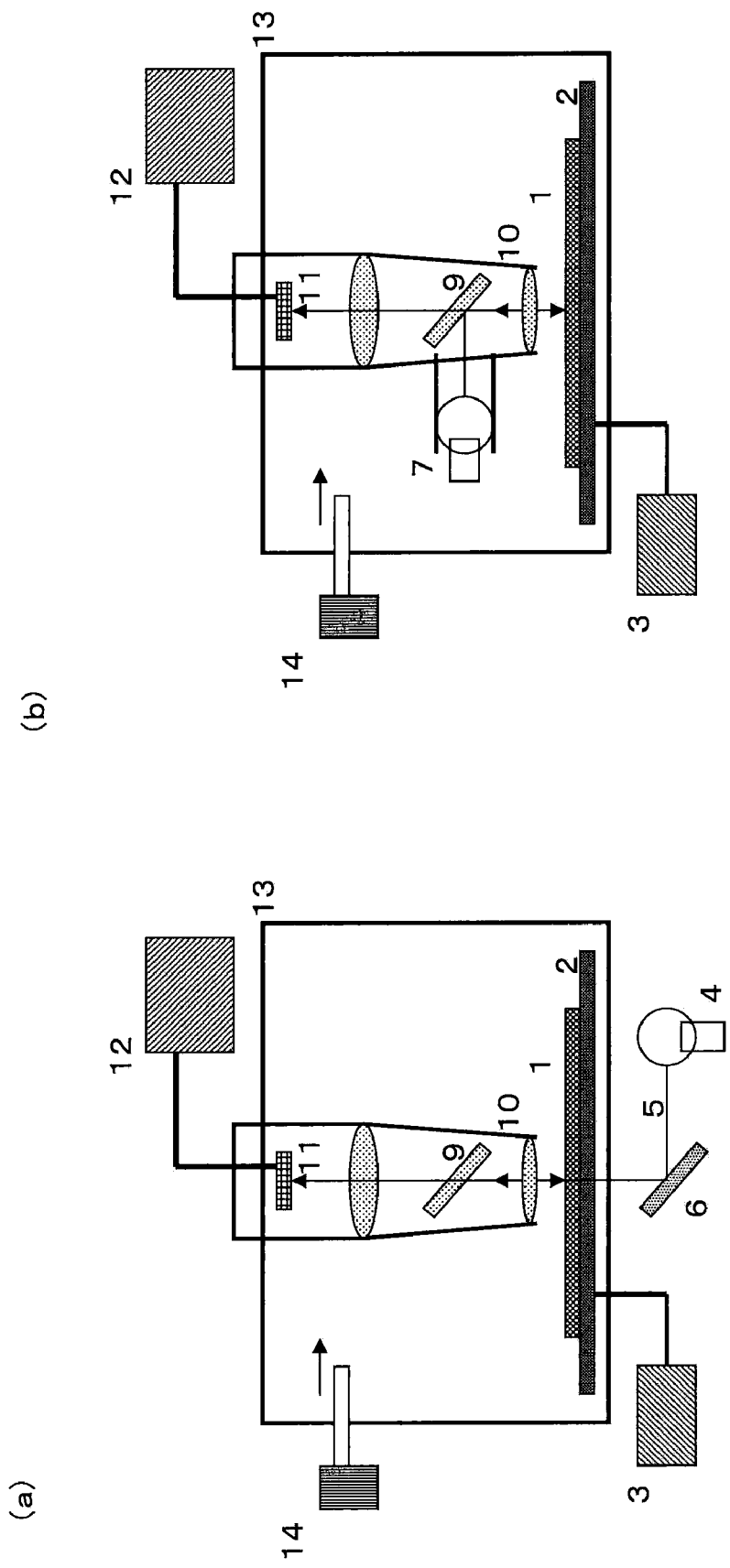
FIGS. 1(a), (b) are schematic diagrams of an organic electroluminescence element defect inspection apparatus of a first embodiment of the present invention.

FIGS. 1 (a), (b) are schematic diagrams of an organic electroluminescence element defect inspection apparatus of a first embodiment of the present invention. (a) is an example of an inspection apparatus which detects a defect using transmitted light. (b) is an example of inspection apparatus which detects a defect using reflected light. Each inspection apparatus of FIG. 1 provides an inspected substrate 1 on a stage 2 controlled by a driving mechanism 3 and infrared light from a transmitted illumination of an infra-red radiation optical source 4 or from a reflected optical source of an infra-red radiation optical source 7 is delivered to an inspected substrate 1 through a mirror 6 or a half mirror 9. The optical image is brought in by an infra-red radiation image sensor 11 through a lens 10 and an image brought in by an image sensor 11 is processed by an image processing apparatus 12. Moreover, whether there is a defect on a substrate is determined and whether a substrate is acceptable is inspected.

Either a transmitted optical source or a reflected optical source can be used for an optical source, if infra-red radiation is used. However, because a layer thickness of a formed organic luminescent layer is very thin, the amount of optical absorption is small. Therefore, a reflected optical source where reflected light passes twice on a surface of a substrate is more preferable than a transmitted optical source where a light beam passes a layer once, since a contrast can be easily provided. Moreover, the infra-red radiation which is used has no special restrictions, if the used infra-red radiation has a wavelength area which is sensitive to an image sensor. However, if a wavelength is too long, the resolution of an image is poor. Therefore, the wavelength of the inspection light is preferred to be 700~1500 nm. And an image sensor can be either an area sensor or a line sensor. In addition, in FIG. 1, only one image sensor is shown, however, a plurality of image sensors can be arranged in a line to reduce inspection time and a defect inspection may be performed.

In addition, because a thin layer of an organic electroluminescence layer may be degraded by visible light, degradation is prevented by intercepting light from the entire inspection apparatus of an organic electroluminescence element defect inspection apparatus of a first embodiment of the present invention by an interception enclosure 13.

Moreover, because a thin layer of an organic luminescent layer is easily degraded by oxygen or moisture in the air, it is necessary to reduce the time during which the organic luminescent layer is exposed to the air as much as possible. Purging by an inactive gas is effective in separating an organic luminescent layer from the air. In the case where a process of forming an organic luminescent layer such as a print or an ink jet is performed in the air, purging by an inactive gas is necessary for an inspection in a process. Therefore, an inactive gas is injected into the enclosure 13 from an inactive gas injecting hole 14 to purge the air in the enclosure. An inactive gas is not restricted as long as the inactive gas does not damage an organic luminescent layer. However, nitrogen is preferably used in terms of cost and safety.

Figure 2:
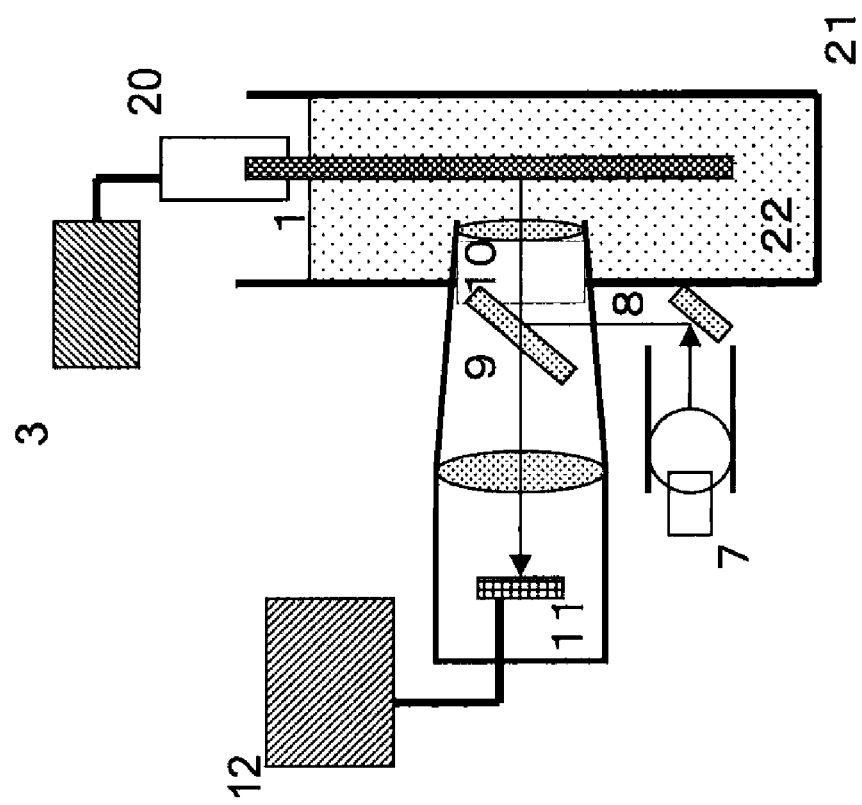
FIG. 2 is a schematic diagram of an organic electroluminescence element defect inspection apparatus of a second embodiment of the present invention.

FIG. 2 is a schematic diagram of an organic electroluminescence element defect inspection apparatus of a second embodiment of the present invention. In FIG. 2, an inspected substrate 1 is provided to a substrate retainment section 20 which is controlled by a driving mechanism 3. And with a condition that the inspected substrate 1 is dipped in an inactive liquid 22 and is separated from the air, the inspected substrate 1 is irradiated with infrared light from a reflected optical source of an infra-red radiation optical source 7 through a half mirror 9. The optical image is brought in by an infra-red radiation image sensor 11 through a lens 10. The image brought in by the image sensor 11 is processed in an image processing apparatus 12. And whether there is a defect on the substrate is determined and whether the substrate is acceptable is inspected.

As an organic electroluminescence element defect inspection apparatus of a second embodiment of the present invention showed in FIG. 2, when an inspection is performed under the condition that an inspected substrate is dipped in an inactive liquid and separated from the air, time loss is reduced compared with a purge by an inactive gas. Liquid which does not melt or damage an organic luminescent layer can be used as an inactive liquid, for example, hydrophobic solvents such as alkane, ether and ester, liquid matter of fluorine compounds such as fluoroether and fluoroalkane. In particular, fluorine compounds do not damage an organic luminescent layer such as a melting and in addition, vapor pressure of a fluorine compound is relatively high and a fluorine compound is dried off immediately after an inspection. Therefore, a fluorine compound is preferably used.

Figure 3:
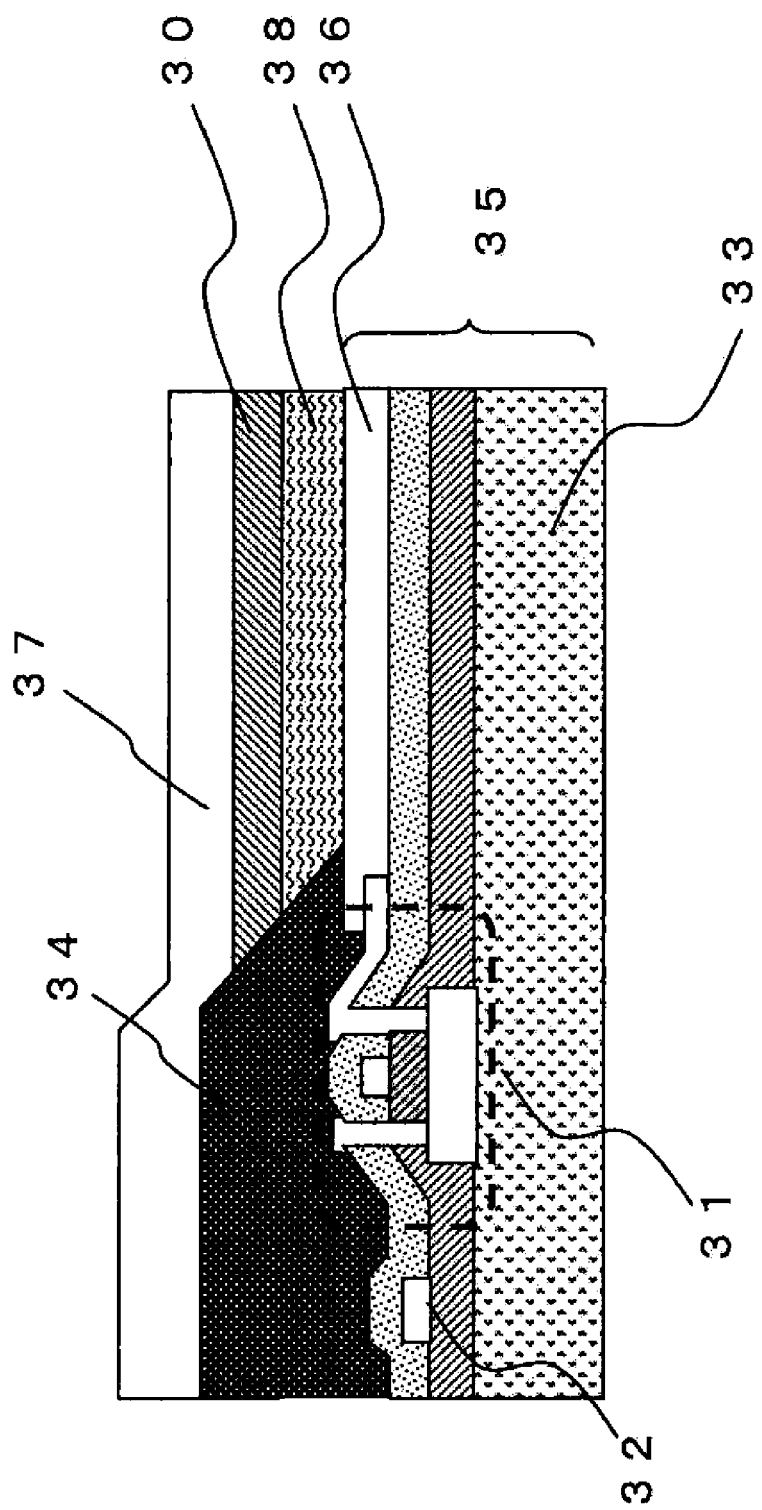
FIG. 3 is a schematic diagram of an organic electroluminescence element defect inspection apparatus.

FIG. 3 is a schematic diagram of an organic electroluminescence element of the present invention. A metal wiring 32 for sending a driving signal to a switching element 31 such as a TFT (Thin Film Transistor) connected to a patterned organic luminescent layer is arranged on a substrate 35 on which an organic luminescent layer 30 is formed. And a metal wiring for sending an electric current controlled by a switching element to an EL element 31 is also arranged on the above substrate. (These metal wirings together are called driving circuit wiring.) Moreover, a confining wall 34 is arranged to prevent a short with an adjacent picture element on these wirings and to upgrade patterning accuracy at the time of printing. One or more organic luminescent layers including a luminescence area, an anode 36 injecting a hole into the organic luminescent layer and a cathode 37 injecting an electrode into the organic luminescent layer are arranged on the substrate. A luminescent medium layer such as a hole transport layer 38, an electric transport layer and an inter layer may be layered between the cathode and the anode, if necessary.

For organic luminescent materials forming organic luminescent layers, the materials which are made by scattering a luminous pigment in high molecule can be used. Coumarin system, perylene system, a pyran system, anthrone system, porufiren system, quinacridon system, N,N'-dialkyl permutation quinacridon system, naphthalimido system, N,N'-diaryl permutation pyrrolo pyrrole series and iridium complex system are examples of the luminous pigments. And polystyrene, polymethyl methacrylate and polyvinyl carbazole are examples of the high molecules. Or, high molecular materials such as poly arylene system, polyarylenevinylene system or a poly fluorene system can be used for the organic luminescent materials.

An organic luminescent ink is prepared by dissolving or dispersing these organic luminescent materials in a solvent. For a solvent in which an organic luminescent material is dissolved or dispersed, toluene, xylene, acetone, anisole, methyl ethyl ketone, methyl isobutyl ketone and cyclohexanone can be used. The above mentioned solvents may be used alone. In addition, the above mentioned solvents may be used as a mixed solvent. Above all, aromatic organic solvents such as toluene, xylene and anisole are preferred from an aspect of solubility of an organic luminescent material. In addition, a surface active agent, an antioxidant, a viscosity modifier, an ultraviolet absorber may be added to an organic luminescent ink as necessary.

In addition to the above described organic luminescent ink materials, a low molecular luminescent material can be used. For example, 9,10-diaryl anthracenes, pyrene, coronene, perylene, rubrene, 1,1,4,4-tetraphenylbutadiene, tris(8-hydroxyquinolonate)aluminum complex tris(4-methyl-8-hydroxyquinolonate)aluminum complex, bis(8-hydroxyquinolonate)zinc complex, tris(4-methyl-5-trifluoromethyl-8-hydroxyquinolonate)aluminum complex, tris(4-methyl-5-cyano-8-hydroxyquinolonate)4,4-tetra phenylbutadiene, tris(8-hydroxyquinolonate)aluminum complex, tris(4-methyl-8-hydroxyquinolonate)aluminum complex, bis(2-methyl-5-trifluoromethyl-8-quinolinolate)[4-(4-cyanophenyl)phenolate]aluminum complex, bis(2-methyl-5-cyano-8-quinolinolate)[4-(4-cyanophenyl)phenolate]aluminum complex, tris(8-quinolinolate)scandium complex, bis[8-(para-tosyl)aminoquinoline]zinc complex, cadmium complex, 1,2,3,4-tetraphenylcyclopentadiene, poly-2,5-diheptyloxi-para-phenylenevinylene can be used.

For methods of forming an organic luminescent layer 30, the following methods can be used depending on the materials: existing methods for example, a dry method such as resistance heating evaporation method, electron-beam evaporation method, reactivity evaporation method, ion plating method and sputtering method or a wet method such as ink-jet print method, relief printing method, photogravure method and screen method may be used. After an organic luminescent layer is formed, a defect inspection is performed by the heretofore described defect inspection method before an electrode is formed.

When a defect inspection is performed by a reflected illumination image, the above described metal wiring strongly reflects inspection light. Therefore, halation occurs on a metal wiring part on the reflected illumination image which is obtained. Therefore a brightness contrast on a picture element part cannot be successfully provided. Then, an organic electroluminescence element including the above described confining wall 34 which has a function to absorb a wavelength of inspection light is provided. Therefore, halation can be prevented and it is possible to improve inspection accuracy. In this case, it is preferable that a confining wall is formed covering the driving circuit wiring.

Generally, a confining wall of an organic electroluminescence element is formed by performing photolithography to make the confining wall a picture element trace figure using a photosensitive resin such as a novolac system, an acryl system or a polyimide system. To absorb the wavelength of the inspection light, it is necessary that a light-absorptive material such as an infrared absorption pigment (an infrared absorption material) is added to these photosensitive resins beforehand. For an infrared absorption pigment (an infrared absorption material), a well-known material such as anthraquinone series, azo series, aminium series, cyanine system, squarylium series, phthalocyanine system and naphthalocyanine series can be used. And the absorption of inspection light by a confining wall does not have to be performed perfectly but has to be practiced to the extent that halation does not occur. An organic electroluminescence element of a top emission type has a structure in which a transparent electrode is formed last. In this case, since generally an electrode on a substrate is a metal electrode, performing a defect inspection by a reflected illumination image is required. However, depending on the illumination conditions and image processing conditions, a defect inspection can be performed by selecting a condition in which halation caused by a reflection from an electrode does not occur.

According to an organic electroluminescence element defect inspection apparatus of the present invention, a defect inspection apparatus capable of improving the efficiency of a production line can be provided by the following method: during a process of manufacturing an organic electroluminescence element, after a luminescent layer is formed on a substrate, a defect inspection of a luminescent pattern on a substrate is performed promptly, and by detecting a luminescent layer pattern defect, a substrate which has a pattern formation defect can be found. Then a process abnormality can be found promptly. According to an invention of an embodiment of the present invention, an optical source to obtain an optical image from an inspected substrate is infra-red radiation. Therefore, a failure which degrades an electroluminescence element can be prevented by an accumulative irradiation volume of an ultraviolet ray at the time of an inspection.

Moreover, according to an organic electroluminescence element defect inspection apparatus of an embodiment of the present invention, a failure which degrades an organic electroluminescence element such as a reduction in luminescent efficiency and life time can be prevented. However, degradation, which is generated by an irradiation of an ultraviolet radiation or an irradiation of visible light under an oxygen presence during an inspection process, can be prevented because the inspected apparatus has at least one or more methods among each of the method described below. (a) a means of intercepting an inspection stage part which is for taking in an optical image of an inspected substrate from visible light. (b) a means of purging an inspection stage part which is for taking in an optical image of an inspected substrate by an inactive gas. (c) a means of dipping an inspected substrate of an inspection stage part which is for taking in an optical image of an inspected substrate in an inactive liquid Next, an organic electroluminescence element of an embodiment of the present invention has a confining wall covering a driving circuit wiring formed on a substrate. The confining wall can absorb light of a wavelength of an optical source of the above described organic electroluminescence element defect inspection apparatus of an embodiment of the present invention. In other words, the confining wall can absorb infrared light. Therefore, halation by metal wiring which is for sending a driving signal or a control current to an element is prevented, and improving inspection accuracy becomes possible. Thereby, an organic electroluminescence element suitable for an organic electroluminescence element defect inspection apparatus of the present invention can be provided.

In addition, according to an organic electroluminescence element defect inspection method of an embodiment of the present invention, improving efficiency of a production line becomes possible by the following method: during a process of manufacturing an organic electroluminescence element, after a luminescent layer is formed on a substrate, before moving on to a next process, a defect inspection of a luminescent layer pattern on a substrate is practiced promptly; therefore a pattern defect of a luminescent layer can be detected and a substrate which has a pattern formation defect can be detected promptly.

EXAMPLES

Below, specific examples of the present invention are explained.

Example 1

A Defect Inspection Apparatus

Instead of a heat ray cut filter, a band-pass filter of infra-red radiation was arranged on an output stage of a halogen lamp of an optical source of a substrate defect inspection apparatus. The defect inspection apparatus was of an adjacent picture element comparison inspection method. The adjacent picture element comparison inspection method was used as a flat panel display defect inspection apparatus. And the flat panel display was produced by elements such as a TFT or color filter. The inspection light provided was infrared light with a wavelength around 900~1100 nm as a main component.

<Formation of a Substrate to be Printed>

A TFT substrate of a bottom emission type was prepared and a positive type photo-sensitive polyimide photoneece DL-1000 (manufactured by Toray Industries, Inc.) including 2% by weight of YKR-3070 (manufactured by Yamamoto Chemicals, Inc.) as a near-infrared absorption pigment was used as a photoresist material used for forming a confining wall. Next, the photoresist material was coated on the TFT substrate by a spin coat. After spinning for 5 seconds with conditions that spin coat was 150 rpm, spinning of 500 rpm for 20 seconds was performed. And under these conditions, it was coated once. Then, a confining wall of 1.5 µm height was formed. A photo-sensitive material applied thoroughly on a substrate was exposed and developed by a photolithographic method. And a confining wall having a matrix shaped line pattern on a wiring part of a picture element was formed. Next, a confining wall was burned in an oven at 230 degrees Celsius for 30 minutes.

<Formation of an Organic Luminescent Layer>

After the above described substrate to be printed was washed thoroughly with a mild detergent, ultrasonic cleaning was performed for 5 minutes in a detergent solution. Next, after the substrate to be printed was rinsed with deionized water thoroughly, ultrasonic cleaning was performed for 10 minutes in deionized water. After washing, moisture on the substrate was dried adequately under IPA (isopropyl alcohol) saturated vapor. 1.5 wt % aqueous solution (CH8000 manufactured by H.C. Starck GmbH) of poly(3,4-ethylenedioxythiophene) and polystyrene sulfonic acid (PEDOT/PSS) as a hole transport layer was applied by a spin coat method and baked on the substrate. And a thin layer with a thickness of 40 nm was formed. A substrate to be printed was formed in this way.

In addition, a plate material having 0.3 mm of a polyamide system photosensitive resin layer on a metal substrate material with a thickness of 0.2 mm including an alloy of iron and nickel having 36% of nickel was prepared. The plate material was exposed through a photomask and water-developed. A relief printing plate having a convex pattern of a stripe shape was provided in this way. And a line width of a convex part of a relief printing plate which was obtained was 100 μm and a pitch of 350 μm.

Next, an organic luminescent ink having three colors of red (R), green (G) and blue (B) was prepared. A red luminescence ink (R): a solution dissolving 1% by mass of polyfluorene derivative in toluene. (A red luminescence material manufactured by Sumitomo Chemical Co., Ltd. . . . name of commodity is Red 1100). A green luminescence ink (R): a solution dissolving 1% of by mass of polyfluorene derivative in toluene. (A green luminescence material manufactured by Sumitomo Chemical Co., Ltd. . . . name of commodity is Green 1100). A blue luminescence ink (R): a solution dissolving 1% of by mass of polyfluorene derivative in toluene. (A blue luminescence material manufactured by Sumitomo Chemical Co., Ltd. . . . name of commodity is Blue 1100). The above-mentioned relief printing plate was fixed to a single-substrate processing type relief printing apparatus. Printing of each color was performed on the substrate to be printed by using this apparatus and the above-mentioned organic luminescence ink. Organic luminescent layers were printed so that a red organic luminescent layer, a green organic luminescent layer and a blue organic luminescent layer line up in the shape of stripes.

<An Image Inspection>

An image inspection of a provided TFT substrate on which an organic luminescent layer pattern was formed as shown above was performed by the above described infra-red radiation defect inspection apparatus. Then, a contrast on a coaxial vertical illumination image was provided depending on a presence or non-presence of an organic luminescent layer. Therefore, it was possible to perform a defect inspection by comparing brightness values between adjacent picture elements in an image processed for an inspection determination.

A substrate upon which a defect inspection was performed was dried in an inert oven at 130 degrees Celsius for 1 hour. After drying, Calcium (Ca) of 10 nm film thickness was formed on the organic luminescent layer which was formed by printing. Further, argentum (Ag) of 300 nm film thickness was formed thereon. A cathode including Ca and Ag was formed by a vacuum evaporation method. Finally, sealing was performed using a glass cap, thereby a full-colored organic electroluminescence element of the present invention was manufactured.

The organic electroluminescence element was connected to a driving driver, and the luminescent characteristics were confirmed. Then, uniform luminescence of a panel brightness of 900 cd/m$^2$ with a picture element application voltage of 5V was provided. As a Comparative Example 1, an organic electroluminescence element for which a defect inspection was not performed was formed and the element characteristics were compared. Then, the differences caused by a presence or non-presence of an infrared radiation illumination by an inspection were not observed, if the element does not include a defect.

Example 2

A positive type photo-sensitive polyimide photoneece DL-1000 (manufactured by Toray Industries, Inc.) including, as a confining wall formation material, 2% by weight of a near-infrared absorption pigment YKR-3070 (manufactured by Yamamoto Chemicals, Inc.) was used as a photoresist material used for forming a confining wall. Except the above, an organic electroluminescence element was formed in the same way as Example 1. At the stage where an organic luminescent layer was formed, an image inspection was performed by the above described infra-red radiation defect inspection apparatus. Then, a contrast on a coaxial vertical illumination image was provided depending on a presence or non-presence of an organic luminescent layer. Thus, it was possible to perform a defect inspection by comparing brightness values between adjacent picture elements in an image processed for an inspection determination. In Example 2, a metal wiring part is covered with a confining wall having near-infrared absorption characteristics. Therefore, an inspected image having high contrast could be obtained without generating halation, even if the intensity of the illumination is large.

Comparative Example

In addition, as a Comparative Example 2, an organic electroluminescence element was formed in the same way as in Example 1. A difference between Example 1 and this comparative example is that a general halogen lamp was used as an optical source in this Comparative Example of the present invention and not an infra-red radiation optical source at the time of performing a defect inspection. At this time, when an image used for an inspection was photographed by visible light of halogen lamp, an organic luminescent layer pattern on an inspected substrate had little contrast, compared with an infra-red radiation inspected image of the Example. Therefore, it was difficult to confirm a defect in either a coaxial vertical image or a transmitted image. In addition, an organic electroluminescence element formed by a substrate into which inspection light was irradiated was formed and connected to a driving driver. Then, when the luminescence characteristics were confirmed, only a panel brightness of 25 cd/m$^2$ at 5V was obtained suggesting that its capability had degraded.

What is claimed is:

1. An organic electroluminescence element on a substrate, the element comprising:
   one or more organic luminescent layers having a luminescence area;
   an anode which injects a hole into said one or more organic luminescent layers;

a cathode which injects an electron into said one or more organic luminescent layers; and a confining wall formed on said substrate, said confining wall absorbing infra-red radiation, wherein said confining wall covers a drive circuit wiring and a thin film transistor and said confining wall has a matrix shaped line pattern on a wiring part of a picture element.

2. The organic electroluminescence element according to claim 1, wherein said confining wall comprises a photosensitive resin.

3. The organic electroluminescence element according to claim 2, wherein an infrared absorption material is added to said photosensitive resin.

* * * * *